(12) United States Patent
Chasalow

(10) Patent No.: US 6,177,461 B1
(45) Date of Patent: Jan. 23, 2001

(54) PHOSPHOCHOLINATE CARDENOLIDES

(75) Inventor: Fred I. Chasalow, San Carlos, CA (US)

(73) Assignee: Kerix, L.L.C., San Carlos, CA (US)

( * ) Notice: Under 35 U.S.C. 154(b), the term of this patent shall be extended for 0 days.

(21) Appl. No.: 09/534,702

(22) Filed: Mar. 24, 2000

Related U.S. Application Data

(63) Continuation of application No. 09/180,637, filed as application No. PCT/US97/10188 on May 28, 1997.
(60) Provisional application No. 60/018,458, filed on May 28, 1996.

(51) Int. Cl.[7] .............................. A61K 31/21; C07F 9/02
(52) U.S. Cl. ............................................ 514/506; 558/166
(58) Field of Search .............................. 568/166; 514/506

(56) References Cited

U.S. PATENT DOCUMENTS 5,663,405 * 9/1997 Ohtani et al. .................... 558/166
5,776,915 * 7/1998 Peterson et al. ................. 558/166

* cited by examiner

*Primary Examiner*—Amelia Owens
(74) *Attorney, Agent, or Firm*—Darby & Darby

(57) ABSTRACT

Disclosed herein are cardenolides and related compounds covalently linked to phosphocholine moieties and pharmaceutical formulations comprising such compounds. Also disclosed herein are methods for treating hypertension, premenstrual syndrome (PMS), preeclampsia and polycystic kidney disease using the compounds.

5 Claims, 17 Drawing Sheets

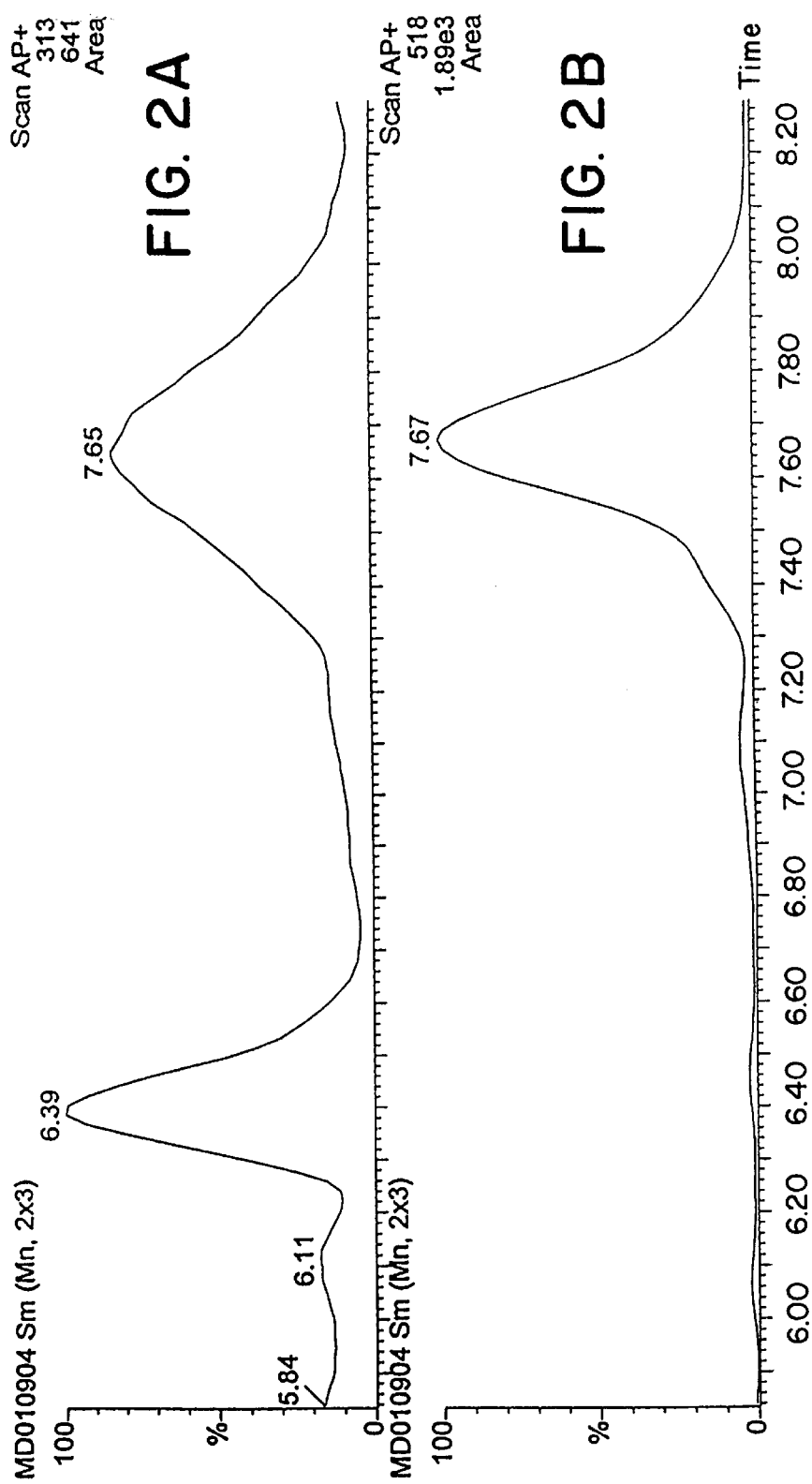

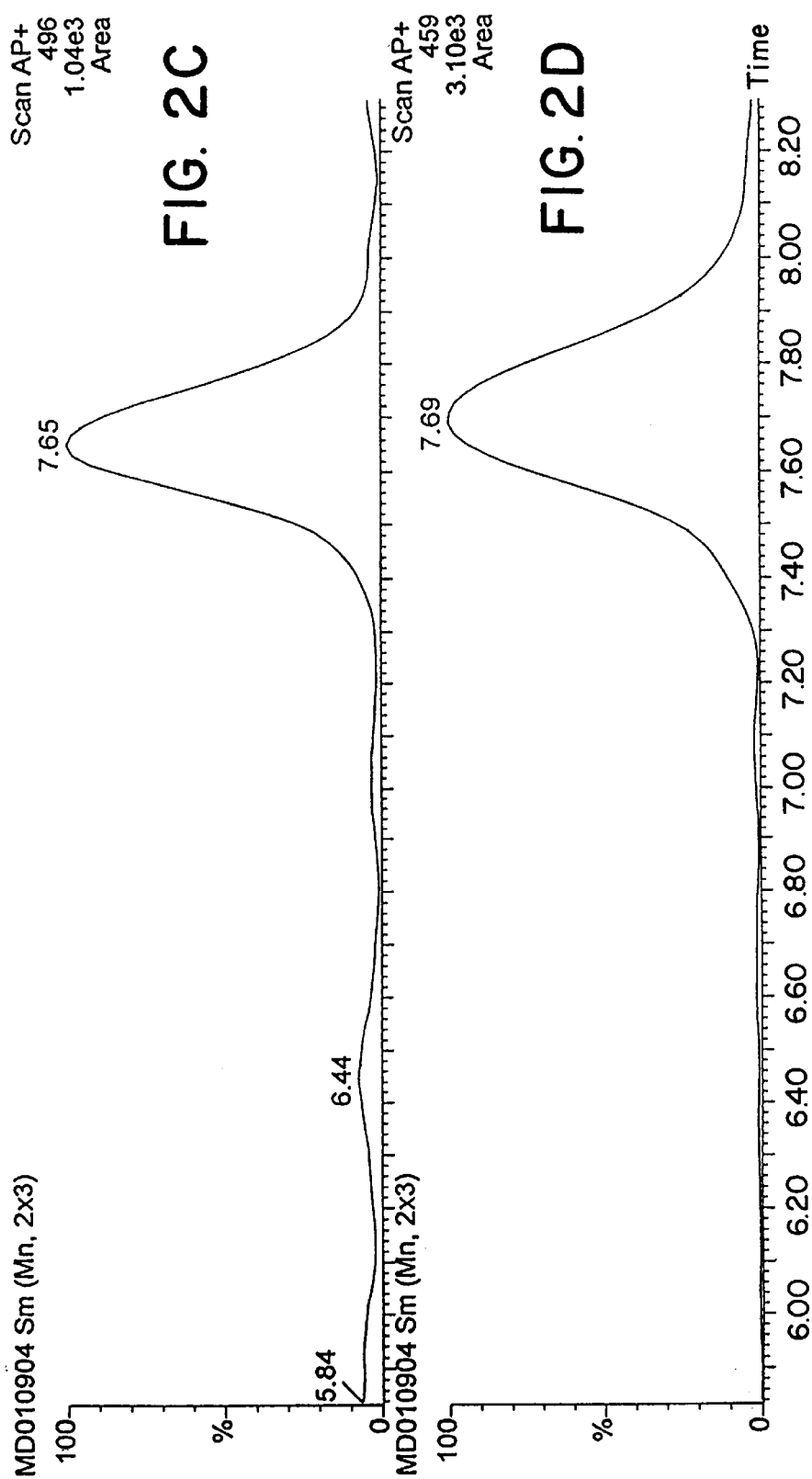

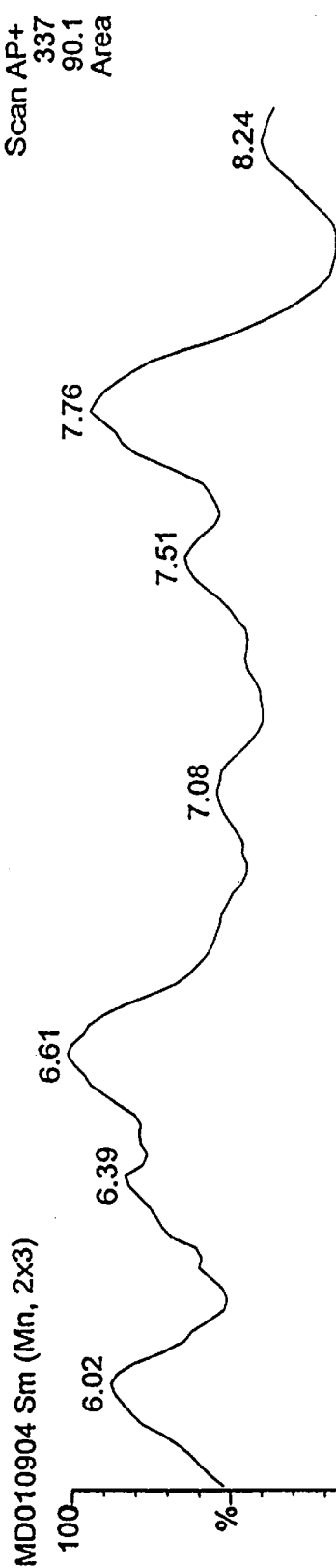
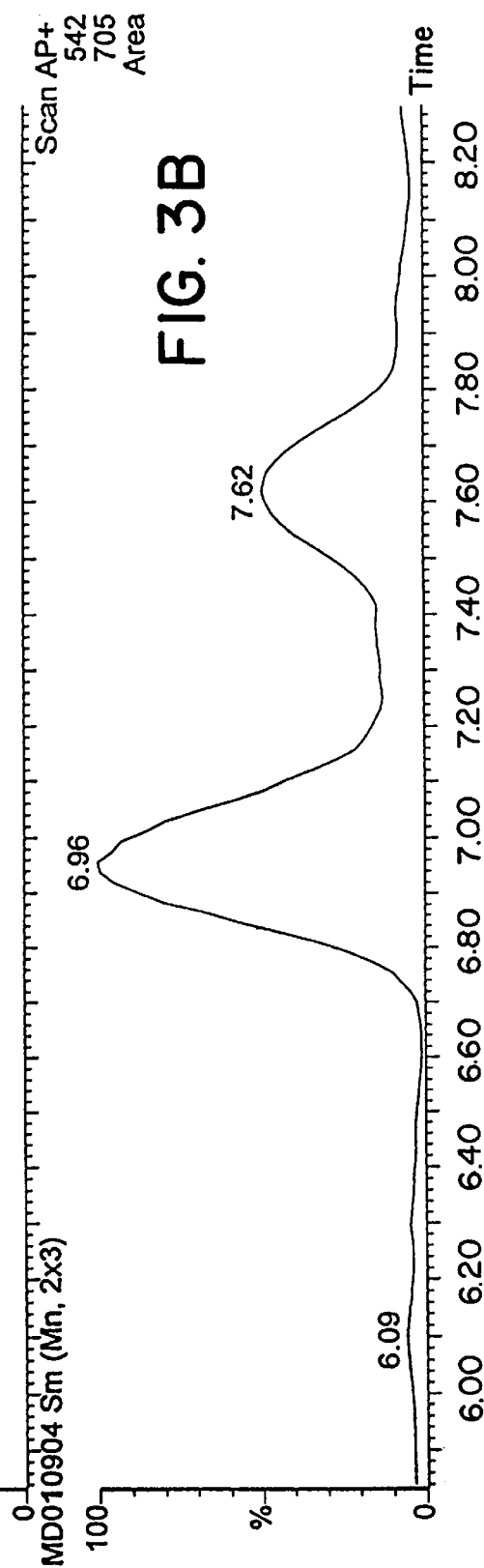

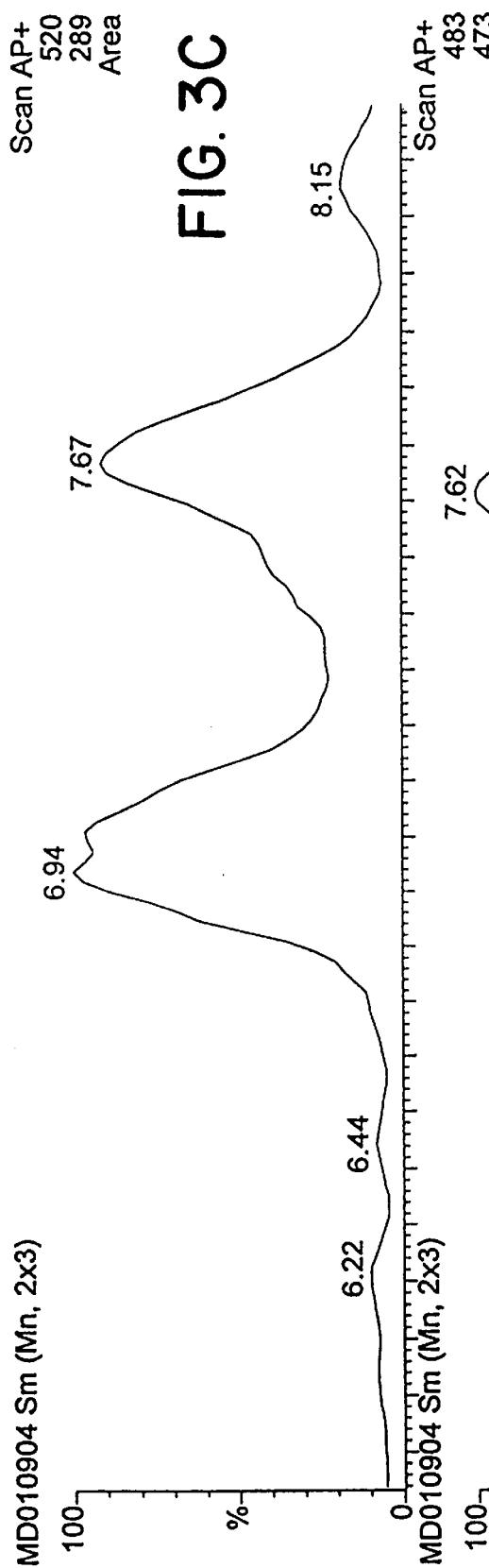
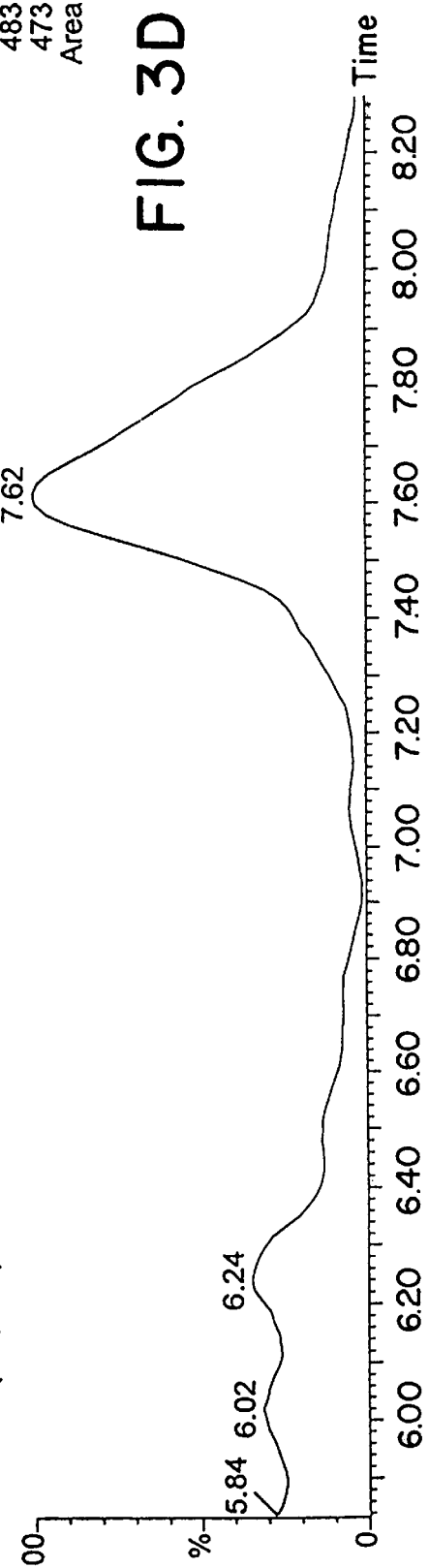
FIG. 3C
FIG. 3D

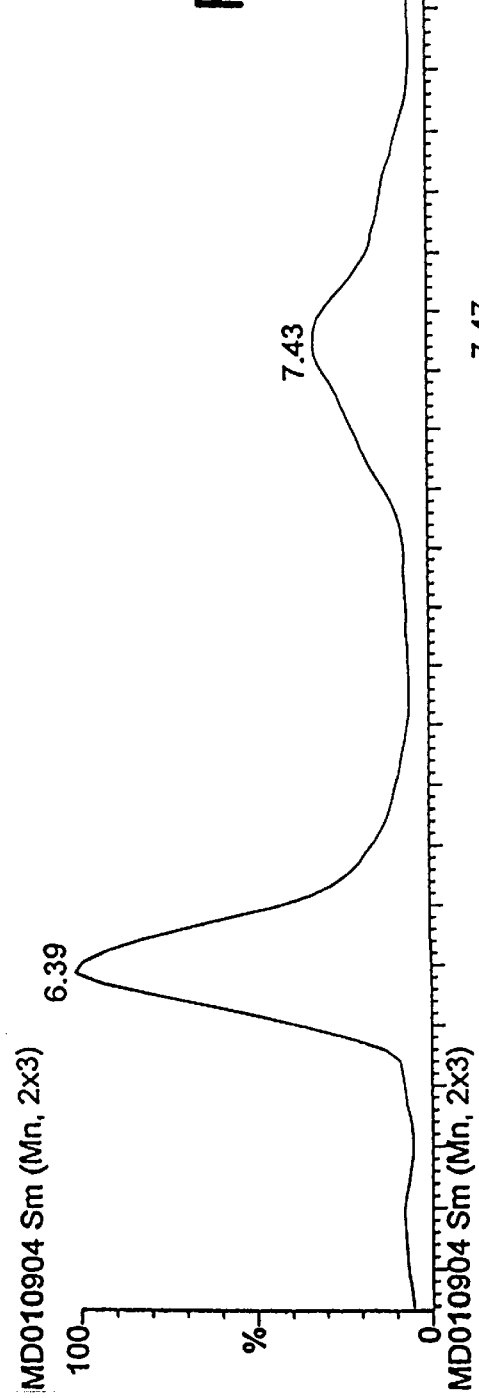
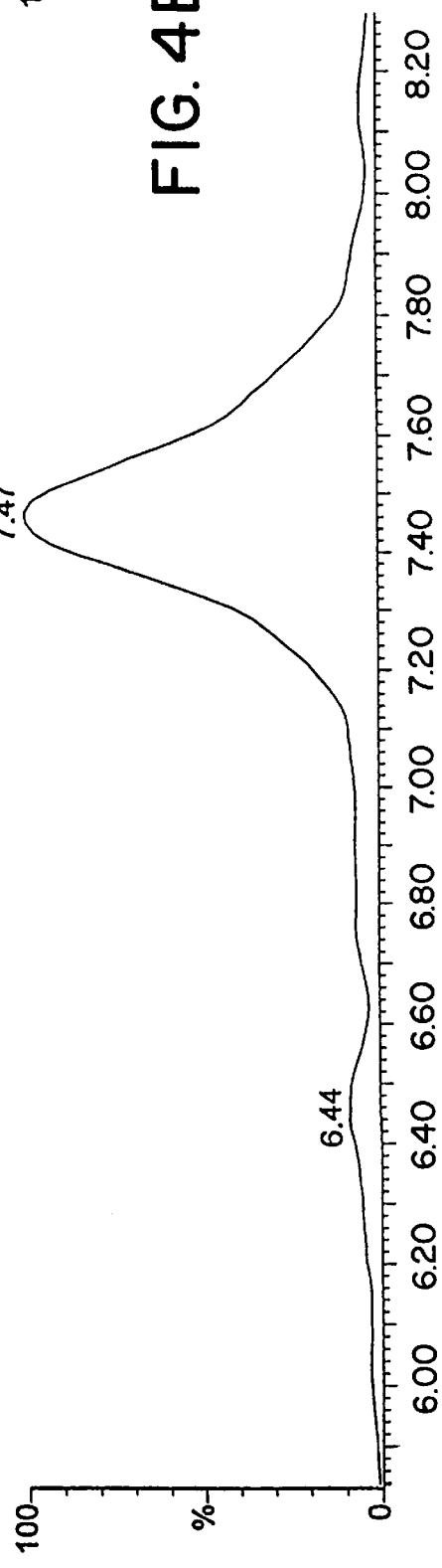

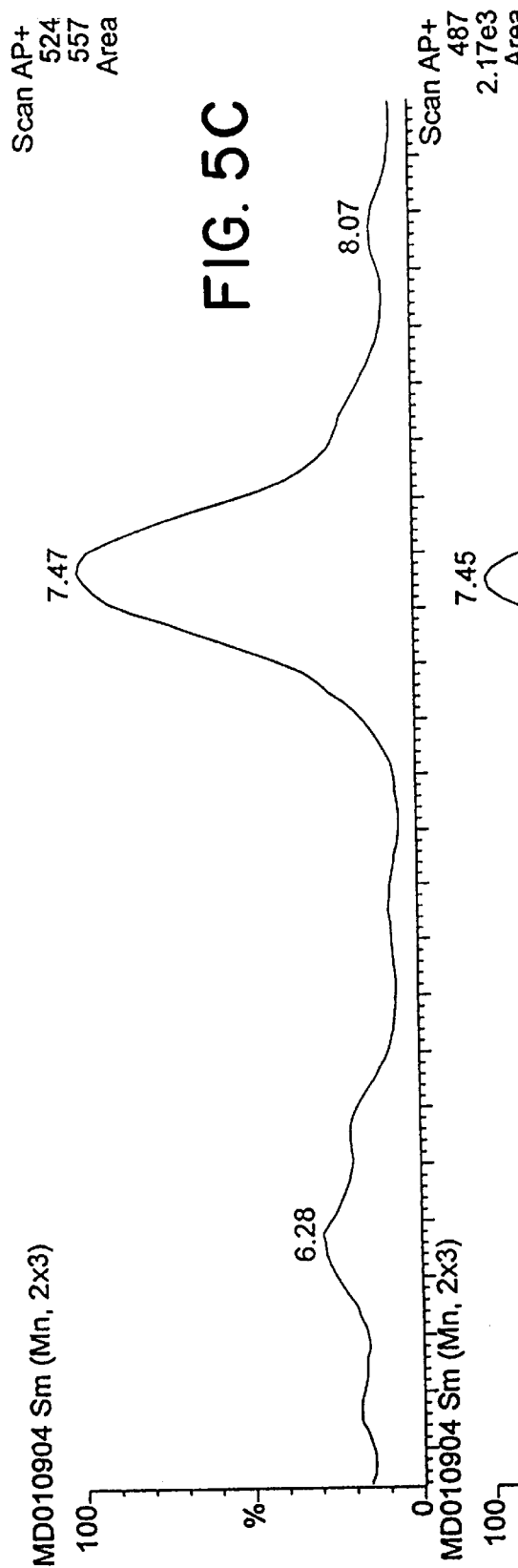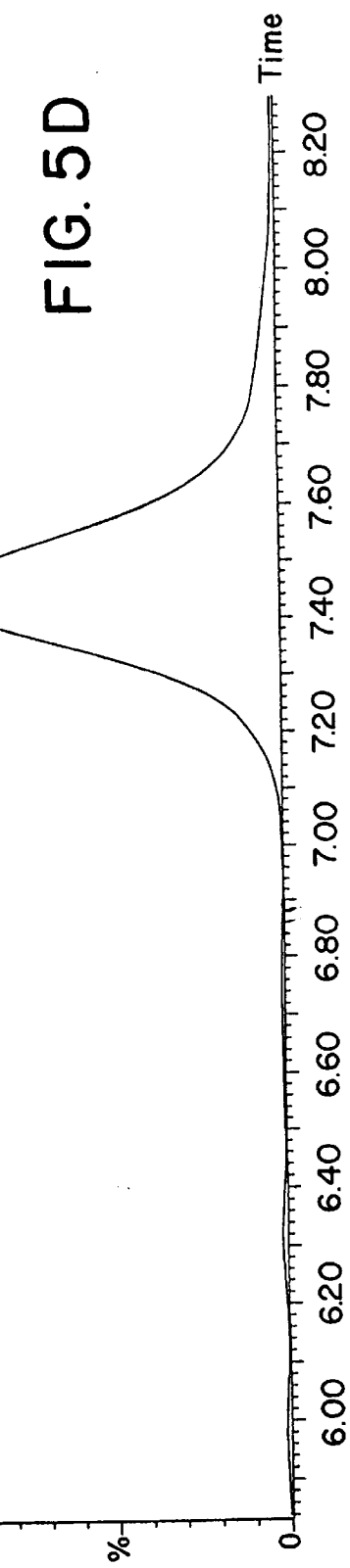

PHOSPHOCHOLINATE CARDENOLIDES

This is a continuation of application Ser. No. 09/180,637, filed Jan. 21, 1999 which is a 371 of PCT/US97/10188, filed May 28, 1997. Each of these prior applications is hereby incorporated herein by reference, in its entirety.

This application claims priority pursuant to 35 U.S.C. §119 from U.S. application Ser. No. 60/018,458 filed May 28, 1996, the entire disclosure of which is hereby incorporated by reference.

FIELD OF THE INVENTION

This invention is related to cardenolides and related compounds covalently linked to phosphocholine moieties, pharmaceutical formulations comprising such compounds and their therapeutic and diagnostic use.

BACKGROUND OF THE INVENTION

Digoxin, digitalis and related cardiotonic agents act on the heart in a variety of ways resulting in an increase in the force of contraction (a positive inotropic effect), a slowing in the rate of atrioventricular conduction thereby leading to improved hemodynamics and renal function. Such agents are useful in treating congestive heart disease and atrial fibrillation.

Congestive heart disease is characterized by an incomplete emptying of blood from the heart during ventricular contraction, which leads to an enlargement of the heart. When congestive heart disease is treated with cardiac glycosides there is a reduction of heart rate, a more complete filling of the ventricules, and the size of the heart decreases and begins to return to normal. Atrial fibrillation is a condition in which the atria contract much more often then the ventricules, causing the lower heart chambers to be bombarded by impulses. The ventricules respond by weakly and inefficiently contracting. When used to treat atrial fibrillation, cardiac glycosides depress the conduction rate, slowing the rate of ventricular contraction and reestablishing a synchronous and effective heart beat.

One of the drawbacks of digoxin and related cardiotonic agents is their low therapeutic index. There is a narrow window of concentrations in which the drugs are effective for the treatment of congestive heart failure or atrial fibrillation. In addition, there are numerous adverse side effects resulting from therapy with digoxin and related compounds. These have been extensively reviewed by T. B. Smith et al. in *Prog. Cardivas. Dis.* 26:21–56, 1984. Side effects of digoxin therapy include impotence, weakness and depression. A further drawback is that some patients do not respond to digoxin treatment. Furthermore, digoxin and digitalis are only effective to depress blood pressure in patients that have previously suffered congestive heart failure and are ineffective in normal hypertensive patients.

Hypertension is a common condition and is characterized by elevations of atrial pressure which could result in secondary organ damage and a reduced life span. The condition is currently treated using four general classes of drugs: diuretics, anti-adrenergic agents, vasodialtors and angiotensin blockers (*Harrison's Principles of Internal Medicine*, K. J. Issel Bacher et al., eds., pp. 1172–1176, McGraw Hill, New York, 1980). Each of these agents produce side effects and their use is limited. Cardiac glycosides, used to treat congestive heart disease, are essentially ineffective in treating hypertension.

Numerous investigators have reported the existence of endogenous digoxin-like factors isolated from various biological fluids. For example, Tymiak, A. K. et al. (*Proc. Nat. Acad. Sci. USA* 9:8189–8193, 1993) disclosed a ouabain-like agent isolated from bovine hypothalamus. Goto, A. et al. (*Clin. Chem* 36:161–162, 1992) also reported finding a ouabain-like factor in human urine and bovine plasma. Shaikh, I. M. et al. (*J. Biol. Chem.* 2:13972–13978, 1991) disclosed a digoxin-like immunoreactive factor isolated from mammalian adrenal cortex. The factor was said to have a molecular mass of 780 daltons comprised of a 390 dalton aglycone component plus several sugar moieties.

U.S. Pat. Nos. 5,028,438 and 5,122,371 issued Jul. 2, 1991 and Jun. 6, 1992, respectively, describe a biologically active agent having hypotensive activity in mammals. The agent was said to be derived from Type 1 human female breast cyst fluid and to be immunoreactive with digoxin antibodies.

SUMMARY OF THE INVENTION

Figure 1A:
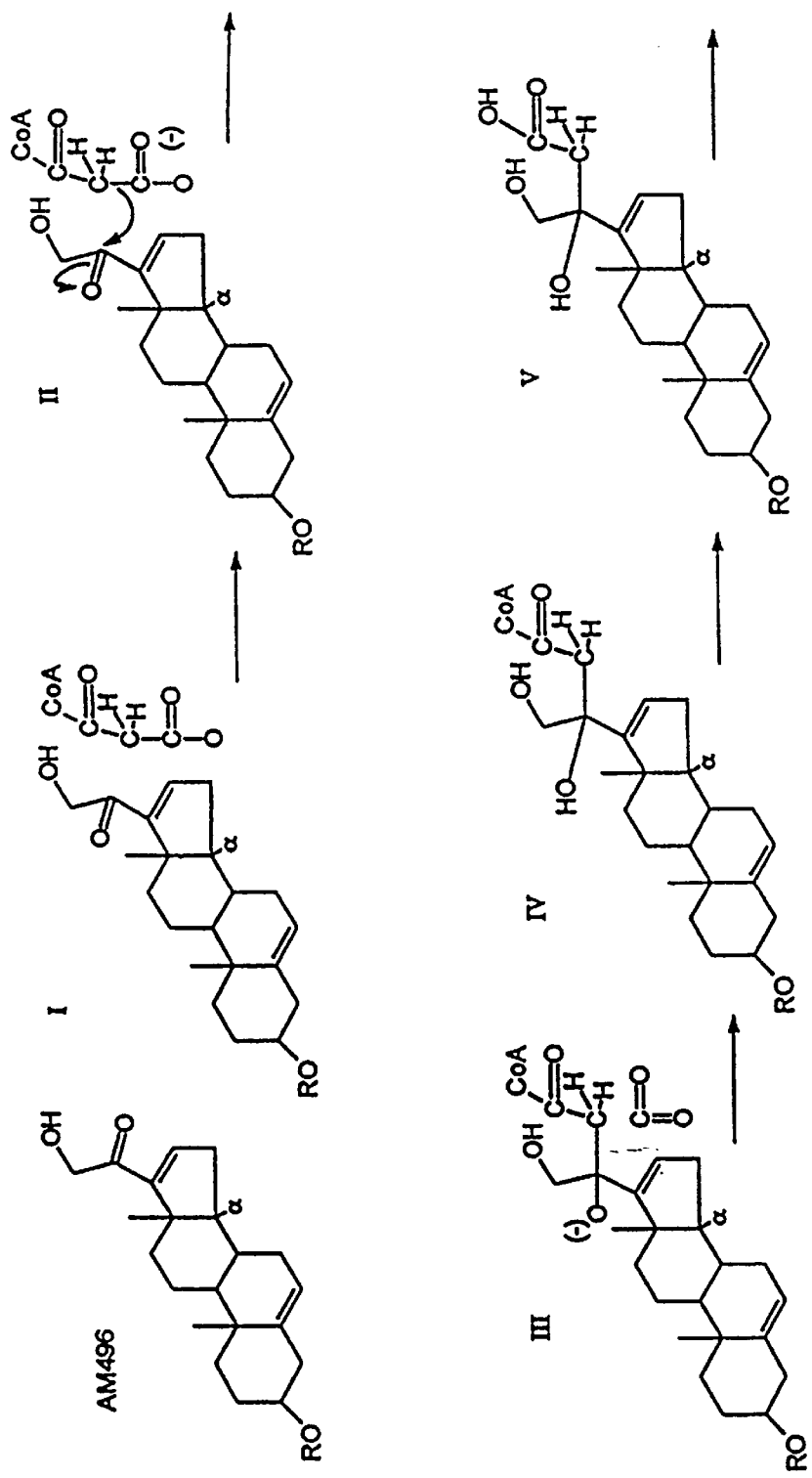
FIG. 1 is a chart showing a proposed pathway for the synthesis of and the inter-relationship between the compounds of the present invention.

Phosphocholinate cardenolides having anti-hypertensive activity in mammals and related phosphocholinate compounds have now been unexpectedly discovered. Analysis of the levels of these compounds in serum can be used to diagnose hypertension in mammals. These compounds can be obtained and used to treat hypertension in mammals.

In one aspect, the present invention is directed to compounds having the formula

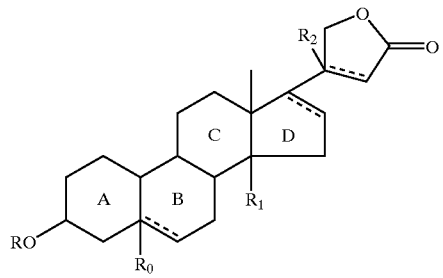

wherein R=phosphocholine wherein $R_2$=OH or H, if dashed line is absent wherein the dashed lines represent a double bond which may be present or absent, and (a) if present in ring B, $R_0$ is absent; (b) if absent, $R_0$ is H-$\beta$, $R_1$ is $\alpha$-H or $\beta$-H.

In another aspect, the present invention is directed to compounds having the formula

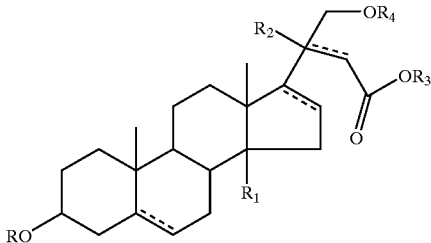

wherein
$R_1 = \alpha$-H or $\beta$-H;
$R_2 =$ H or OH;
$R_3 =$ CH$_3$, CH$_2$-CH$_3$, CH(CH)$_2$, n-buytl or other alkyl group;
$R_4 =$ H, acetate or other ester; and
R = phosphocholine.

In another aspect the present invention is directed to a method for treating a mammal suffering from hypertension comprising administering an effective amount for treating hypertension of a compound having the formula

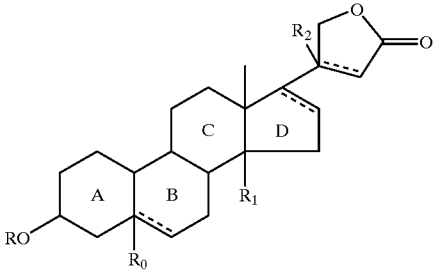

wherein R = phosphocholine
wherein $R_2 =$ OH or H, if dashed line is absent
wherein the dashed lines represent a double bond which may be present or absent, and (a) if present in ring B, $R_0$ is absent; (b) if absent, $R_0$ is H-$\beta$, $R_1$ is $\alpha$-H or $\beta$-H.

In yet another aspect the present invention is directed to a pharmaceutical formulation for treating hypertension in a mammal comprising an isolated compound having the structure

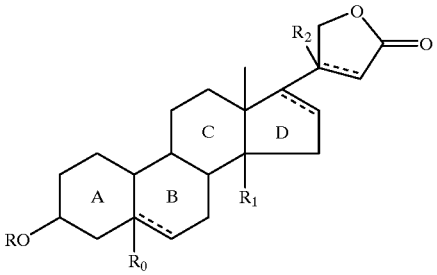

wherein R = phosphocholine
wherein $R_2 =$ OH, if dashed line is absent
wherein the dashed lines represent a double bond which may be present or absent, and (a) if present in ring B, $R_0$ is absent; (b) if absent, $R_0$ is H-$\beta$, $R_1$ is $\alpha$-H or $\beta$-H.
and a pharmaceutically acceptable carrier or diluent.

In a further aspect the present invention is a method for diagnosing hypertension in a patient comprising the steps of:

a) obtaining a serum sample from said patient;
b) determining the amount of a compound selected from the group consisting of AM-496, AM-520, AM-522, AM-524 and AM-540;
c) comparing the amount of said compounds determined in step b with the amount of said compounds present in normotensive individuals;
wherein said patient is suffering from hypertension if the amount of said compounds determined from said patient is significantly different from the amount of said compounds present in said normotensive individuals.

In another aspect the present invention is directed to a method for diagnosing pre-menstrual syndrome (PMS) in a female patient comprising the steps of:

a. obtaining serum samples from said patient during said patient's menstrual cycle;
b. determining the levels of AM-496, AM-520, AM-522, AM-524 and AM-540 in said samples;
c. comparing the levels of said compounds with those present in serum samples obtained from normal female patients not suffering from PMS;
d. wherein the levels in any one of said compounds is significantly different in said patient compared to said normal controls, said female patient is suffering from PMS.

In another aspect the present invention is directed to a method for treating a mammal suffering from polycystic kidney disease comprising administering to a mammal in need of such treatment a disease treatment effective amount of AM-524.

These and other aspects of the present invention will be apparent to those of ordinary skill in the art in the light of the present description, claims and drawings.

DETAILED DESCRIPTION OF THE INVENTION

All patent applications, patents and literature references cited in this specification are hereby incorporated by reference in their entirety. In case of any inconsistences, the present disclosure, including definitions, will prevail.

Cardenolide phosphocholinates having the structure (I) and related compounds having the structure (II) have now been unexpectedly discovered.

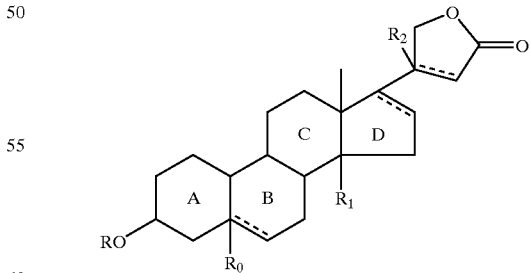

I.

wherein R = phosphocholine
wherein $R_2 =$ OH or H, if dashed line is absent
wherein the dashed lines represent a double bond which may be present or absent, and (a) if present in ring B, $R_0$ is absent; (b) if absent, $R_0$ is H-$\beta$, $R_1$ is $\alpha$-H or $\beta$-H.

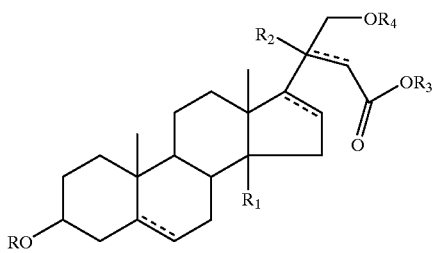

wherein $R_1 = \alpha\text{-H}$ or $\beta\text{-H}$;
$R_2 = \text{H}$ or OH;
$R_3 = \text{CH}_3\text{-CH}_2\text{-CH}_3$, $\text{CH}(\text{CH}_3)_2$, n-buytl or other alkyl group;
$R_4 = \text{H}$, acetate or other ester; and
R=phosphocholine.

The compounds are present in the serum of all mammals tested (human, rat, goat, mouse, pig and cattle). These compounds can be obtained from numerous sources, including without limitation, Type 1 human female breast cyst fluid (obtained by needle biopsy), bovine adrenal extracts and porcine ovarian follicular extracts. Bovine adrenal glands and porcine ovarian follicles can be obtained from commercial slaughter houses. The extracts can be prepared as described below. Human breast cyst fluid can be obtained and identified as set forth in U.S. Pat. No. 5,028,438 issued Jul. 2, 1991.

Figure 1B:
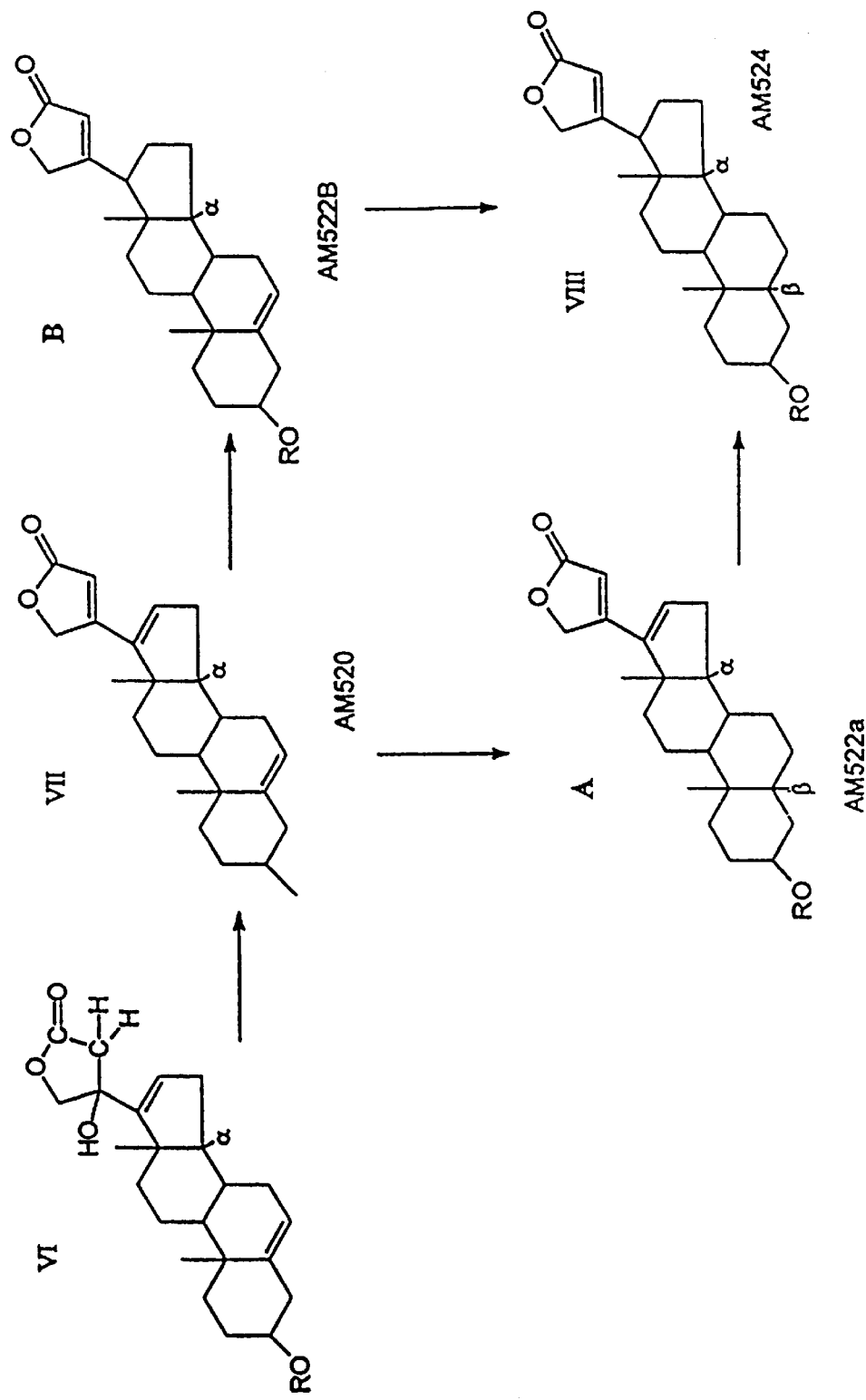

Although the phosphocholinate compounds of the present invention are found in human female breast cyst fluid as a mixture, their structure, interrelationship and physical properties of the individual compounds (indeed, the fact that there are multiple members of the family of compounds—see FIG. 1) were not apparent from the disclosure of U.S. Pat. Nos. 5,028,438 and 5,122,371. Phosphocholinate compounds produced pursuant to the present invention may be isolated and purified from the mixture disclosed in these patents.

The compounds of the present invention, exemplified by AM-520 or γ, AM-522a or AM-522b or β, AM-524 or α for Structure I and AM-496 or δ for Structure II can be isolated as set forth below. α, β and γ are cardenolides with antihypertensive activity in mammals which cross-react with digoxin-specific antibodies. The structures of α, β, γ and δ and their proposed interrelationship is shown in FIG. 1.

When isolated from Type 1 human breast cyst fluid, the compounds may be obtained and purified as set forth in U.S. Pat. No. 5,028,438.

When isolated from tissue (e.g. ovarian follicular tissue or adrenal glands), the tissue is homogenized with a mixture of, by way of non-limiting example, methanol, acetone, ethanol and preferably acetonitrile and water to give a final ratio of between about 10:1 and about 3:1 and preferably about 4:1. Because of the water present in the tissue, adding a 6:1 ratio of solvents leads to a ratio of 4:1 present. The mixture is filtered using, for example, a Whatman #1 filter (or any equivalent) and insoluble material is discarded. The volume of the filtrate is determined and 50% of the volume is added as for example toluene, chloroform and preferably benzene to yield a lower aqueous and an upper organic phase. The lower aqueous phase contains most of the active material but some additional material can be recovered by re-extracting the upper organic phase and combining the aqueous phases. The combined aqueous phases are evaporated to dryness under vacuum, using, by way of non-limiting example, a rotary evaporator without allowing the temperature to exceed about 40° C. The evaporated extract is redissolved in a minimum volume (20–50 ml per liter of original extract) of acetonitrile:methanol:water (4:1:1) and filtered (using, by way of non-limiting example, a Whatman #1 filter) discarding any insoluble materials. Alternatively, the lower aqueous phase can be freeze-dried producing a residue. The freezer-dried residue in this embodiment is dissolved in 20-50 ml per liter of original extract of acetonitrile:water:methanol (4:1:1). Insoluble material is removed by filtration as above. In either case, the filtrate is preparatively chromatographed on a RSIL-NH$_2$ column (Alltech, Chicago, Ill.) (22×500 mm/diameter×length) using an acetonitrile:water:methanol gradient with increasing water concentrations. Alternatively, any amino isopropyl column, such as an amino carbohydrate column (Alltech) can be used. An example of a suitable gradient is set forth below.

| Time (Min) | Acetonitrile | Methanol | Water | Flowrate |
|---|---|---|---|---|
| 0 | 75 | 20 | 5 | 5 ml/min |
| 40 | 65 | 20 | 10 | 5 ml/min |
| 40 | 65 | 20 | 10 | 5 ml/min |
| 80 | 20 | 20 | 60 | 5 ml/min |
| 120 | 20 | 20 | 60 | 5 ml/min |
| 130 | 75 | 20 | 5 | 5 ml/min |
| 180 Stop | 75 | 20 | 5 | 5 ml/min |

Each fraction is analyzed by HPLC and appropriate fractions identified by LC-MS (see below), pooled, lyophilized, redissolved and the preparative procedure may be repeated as necessary until the LC-MS shows that only one material is present. AM-524 and AM-496 have the properties set forth below.

| | AM-524 (α) | AM-496 (δ) |
|---|---|---|
| Physical Properties | | |
| UV absorption maxima | ~230 nm | ~240 nm |
| Molecular weight | 524 daltons | 496 daltons |
| Peaks in mass spectra (APCI+) | 546, 524, 487, 341, 184 | 518, 496, 459, 313, 184 |
| Acetate derivative | yes - 628 daltons | yes - 560 daltons |
| Cross reactivity with digoxin antibodies | Yes | No |
| Assignment of mass fragmentations patterns | | |
| Positive ion spectra: | | |
| Sodium salt | 546 | 518 |
| molecular ion | 524 | 496 |
| loss of trimethylamine from sodium salt | 487 | 459 |
| loss of phosphocholine | 341 | 313 |
| phosphocholine | 184 | 184 |
| Negative ion spectra: | | |
| loss of methyl | 509 | 481 |
| loss of choline | 437 | 409 |

The above-identified compounds can be assayed by HPLC-Mass spectroscopy with monitoring at the different specific mass ions. The assignments of the mass fragmentation patterns of the other compounds of the present invention (e.g. AM-520, AM-522 and AM-540) are set forth in Example 1 below. In this way, each compound of the present invention can be separately isolated and identified as each compound elutes in a separate, distinct fraction on the HPLC gradient. The gradient for the HPLC is 95% acetonitrile: 5% water to 55% acetonitrile: 45% water. Varian (Palo Alto, Calif.) HPLC equipment can be used such as model 9010 or 9012 pumps, model 9065 diode array detector (model 9050 single wavelength detector for preparative HPLC and for the monitor on the mass spectrometer), and model 9100 for the autosampler.

The compounds of the present invention can be used in a method for diagnosing hypertension in a patient. The method comprises obtaining a serum sample (i.e. as little as 0.5 ml) from a patient and determining the levels of AM-496, AM-520, AM-522, AM-524 and AM-540 and comparing the levels with those obtained from normotensive (i.e. non-hypertensive) controls. Indeed, ranges of the levels of the compounds can be obtained from normal individuals so that normal controls need not be obtained for each assay. If the amount of any of the compounds of the present invention is significantly different from those of the control group, a positive diagnosis of hypertension can be made. "Significantly different" is defined herein as more than two standard deviations.

Once isolated, the compounds of the present invention can be administered to patients suffering from hypertension, congestive heart disease and atrial fibrillation. When administered to patients suffering from hypertension congestive heart disease and atrial fibrillation, AM-524 is preferred because it should be the most active compound of this series. AM-520 or AM-522 may also be useful because after administration they can be converted in the recipient's body to AM-524.

Without wishing to be bound by theory, it is believed that the compounds of the present invention will have a better therapeutic index than digoxin or digitalis. Because these compounds are endogenous anti-hypertensive agents, it is expected that a metabolic degradative pathway exists that regulates the synthesis and breakdown of these compounds. Therefore, if toxic levels of AM-524 occur, then the degradation pathway will be stimulated thereby reducing the toxicity. In contrast, digoxin and related plant compounds do not have a regulated degradation pathway in mammals and therefore toxic levels can accumulate.

Large amounts of the compounds of the present invention were found in porcine follicular fluid. This fluid should also be the same as that present in human follicles. In women, each month follicles develop, burst to release the ovum to be fertilized and simultaneously release the cardenolides. In one embodiment, the compounds of the present invention can be used to diagnose pre-menstral syndrome (PMS) or administered to women suffering from PMS. Without wishing to be bound by theory it is believed that in some women, inadequate amounts or inappropriate types of the compounds of the present invention are synthesized and released. This would cause sodium and water retention if a Na+-K-ATPase-inhibitory cardenolide of the present invention predominates, features that are part of PMS. This could be diagnosed by measuring serum levels of the compounds described herein during different times (i.e. the beginning, middle and end) of a females menstrual cycle. At the present time, there is no diagnostic laboratory measurement for PMS. If inadequate levels of specific cardenolides were observed, then replacement therapy using the compounds of the present invention would be used once the specific compounds were identified. This therapy would be expected to treat the cyclic edema that is typical of PMS. The natural function of these compounds in the ovary may be to regulate the accumulation of electrolytes and water in the developing follicle. They may also play an important role in the accumulation of amniotic fluid during pregnancy. Without wishing to be bound by theory, AM-496 is expected to be electrolyte and water retaining similar to aldosterone whereas AM-524 should be electrolyte wasting. The cardenolides should cause sodium and water loss if AM-524 predominates.

The characteristic feature of the cardenolide compounds of the present invention is the presence of the phosphocholine group attached to an aglycone. The presence of the phosphocholine group is confirmed by the mass spectral data. The compounds of the present invention are water soluble, but not soluble in most organic solvents such as ethyl acetate, benzene or isoöctane. In the well known Folch solvent mixture (3:4:8, water:methanol:chloroform) these compounds partition into the aqueous phase. The phosphocholinate compounds are all present in high potassium breast cyst fluid (Type 1), follicular fluids, adrenal glands and serum, but are not present or are present in much lower concentrations in high sodium breast cyst fluids (Type 2). The materials are not detectable in testes extracts. Extracts from Type 1 breast cyst fluids containing these compounds were previously shown to cause decreases in blood pressure when administered to rats. The purification process used would have collected each of the phosphocholinate cardenolides described herein as a mixture.

AM-540, AM-524, AM-522 and AM-520 all contain cardenolide groups, similar to the E-ring of ouabain and digoxin, a lactone ring and can be considered as digoxin-like or ouabain-like materials. The cardenolide structures are confirmed by the UV spectra pattern, with absorption at approximately 220 nm (i.e. 220–240 nm), and cross-reactivity with digoxin specific antibodies (commercially available from DuPont, Boston, Mass.).

AM-540, AM-524, AM-522, AM-520 and AM-496 are all present in detectable levels in serum. Measurement of each one will be useful as markers for hypertension, salt accumulation, and in women, cyclic edema or cyclic salt accumulation. As little as 0.5 ml of serum can be used to detect/identify the compounds of the present invention.

There will be patients with both acquired and congenital deficiencies of AM-540, AM-524, AM-522, AM-520 and AM-496. The actual compounds will be useful as replacement therapy for these patients. The phosphocholinate cardenolides will also be useful to treat overdoses of digoxin. A combined digoxin-phosphocholinate cardenolide mixture described further below may also be useful to reduce digoxin-related toxicity. AM-524 is particularly preferred for this use.

It is believed that the compounds of the present invention will alter the activity of the Na+K+-ATPase enzyme. Cardiac glycosides digoxin and digitalis inhibit this enzyme activity. Assays for this activity are shown in Example 3 below.

The compounds of the present invention are endogenous hypotensive agents. For treating mammals afflicted with elevated blood pressure using the compounds of the present invention, the effective dosage of the compounds of this invention depends upon the severity of condition, the stage and the individual characteristics of each mammal being treated. For treating hypertension, congestive heart disease or atrial fibrillation in a mammal, it is expected that the compounds of the present invention will generally be administered in dosages ranging between about 0.01 mg and about 10 mg per kg of body weight per day. As mentioned above, AM-524 is particularly preferred for this use.

The present invention also provides pharmaceutical formulations comprising digoxin and the phosphocholinate cardenolides of the present invention in a combined dosage form. Such dosage forms would have reduced digoxin-related toxicity. AM-524 is particularly preferred for this use. The dosage forms would generally contain about 0.05 mg of digoxin and about 0.01 mg of AM-524.

The compounds of the present invention may be preferably administered orally but can also be administered via the parenteral route, intranasally, sublingually, submucosally or by transdermal patch in pharmaceutical compositions prepared by well known methods. Examples of parenteral dosage forms include aqueous solutions of the compounds of the present invention in isotonic saline, 5% glucose or other well known pharmaceutically acceptable liquids. In a preferred embodiment of the present invention, the pharmaceutical compositions can also be formulated so as to be suitable for oral administration. The active ingredient(s) is contained in a capsule (in liquid form) or a tablet. The quantity of effective dose supplied by each capsule or tablet is relatively unimportant since the total dosage can be reached by administration of either one or a plurality of capsules or tablets or both. The capsules employed may comprise any well known pharmaceutically acceptable material such as gelatin, cellulose derivatives, etc. Each capsule contains an appropriate amount of the compounds of the present invention dissolved in a suitable solvent, e.g. ethyl alcohol USP, purified water USP or any conventional aqueous pharmaceutical material. Due to the increased solubility in aqueous media of the compounds of the present invention the dosage forms can comprise any aqueous pharmaceutical ingredient.

In an alternate embodiment of the present invention, the phosphocholinate compounds of the present invention can be used to treat polycystic kidney disease. Without wishing to be bound by theory, it is believed that polycystic kidney disease leads to an abnormal buildup of some of the intermediate phosphocholinate cardenolide compounds (e.g. AM-520, AM-522, etc.) disclosed herein. It is believed that administration of effective amounts of the end-product (AM-524) will lead to a shutdown of the accumulation of the intermediate compounds and an amelioration of the disease. Such effective amounts can be determined by no more than routine experimentation.

In another embodiment of the present invention preeclampsia can be treated by administering amount of the compounds disclosed herein effective to treat preeclampsia. Preeclampsia is a toxemia of pregnancy characterized by the appearance of a constellation of abnormalities which include hypertension, edema and proteinuria. The effective amounts would be the same used when treating hypertension disclosed above.

The invention is further illustrated in specific examples set forth below which are intended to describe the invention without limiting its scope.

EXAMPLE 1

Proposed Structures of the Compounds of the Present Invention

Proposed structure of AM-496 (δ):
R = Phosphocholine 496 daltons - the mass ion
518 daltons - the sodium salt
459 daltons - loss of NMe3 from choline
313 daltons - loss of phosphocholine

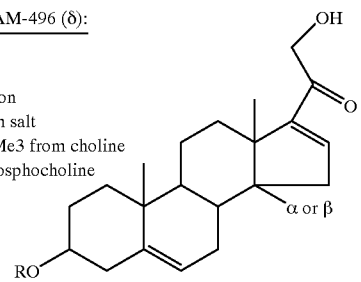

Figure 2E:
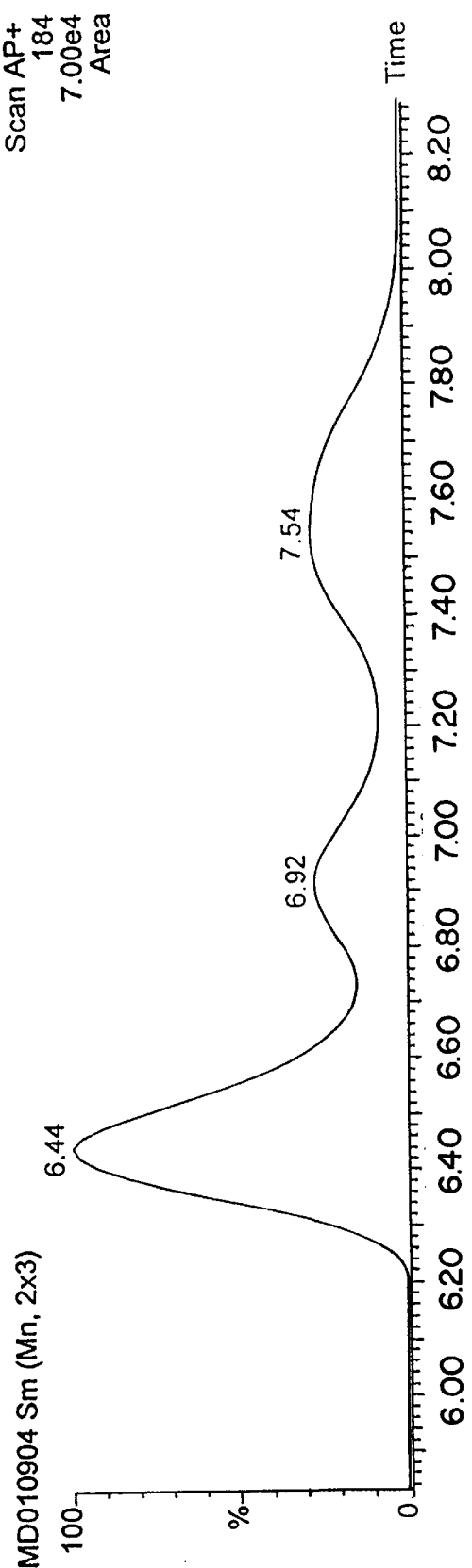
FIG. 2 is the mass spectral data obtained by HPLC/Atmospheric Pressure Chemical Ionization Mass Spectroscopy (HPLC/APCI-MS) on AM-496.

Mass spectral data obtained by APCI+ on column fractions. Chromatograms (FIG. 2) show the coincidence of these fragments in the spectra.

The 313 dalton fragment is the aglycone without the 3 hydroxy group and phosphocholine moiety. The 184 dalton fragment is derived from the phosphocholine. The other fragments confirm the breakdown of the phosphocholine.

The structure was further confirmed by the UV spectrum with a peak at 240 nm as expected for the D-ring conjugated ketone structure. The aglycone portion of the molecule has been reported, but not conjugated to phosphocholine.

When reacted with acetic anhydride in pyridine, a derivative was formed with a mass of 560 daltons. This corresponds to the monoacetate of the sodium salt. The formation of a single acetate ester under these conditions confirms the absence of other exposed hydroxy groups and eliminates sugars at the 3 position.

AM-496 has little cross-reactivity with digoxin-specific antibodies. AM-496 is present in serum from all species tested (human, mouse, rat, goat, cattle).

Functionally, this compound should be a weak aldosterone agonist, similar to 21-hydroxyprogesterone (11-deoxycorticosterone, DOC).

Proposed Structures for AM-520 (γ):
R = Phosphocholine
520 daltons - the mass ion
542 daltons - the sodium salt
483 daltons - loss of NMe3 from choline
337 daltons - loss of phosphocholine

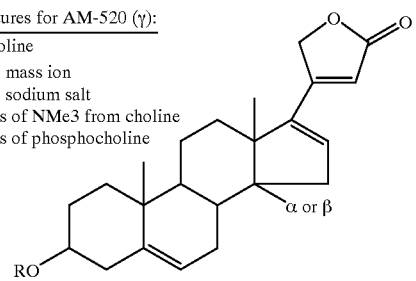

Figure 3E:
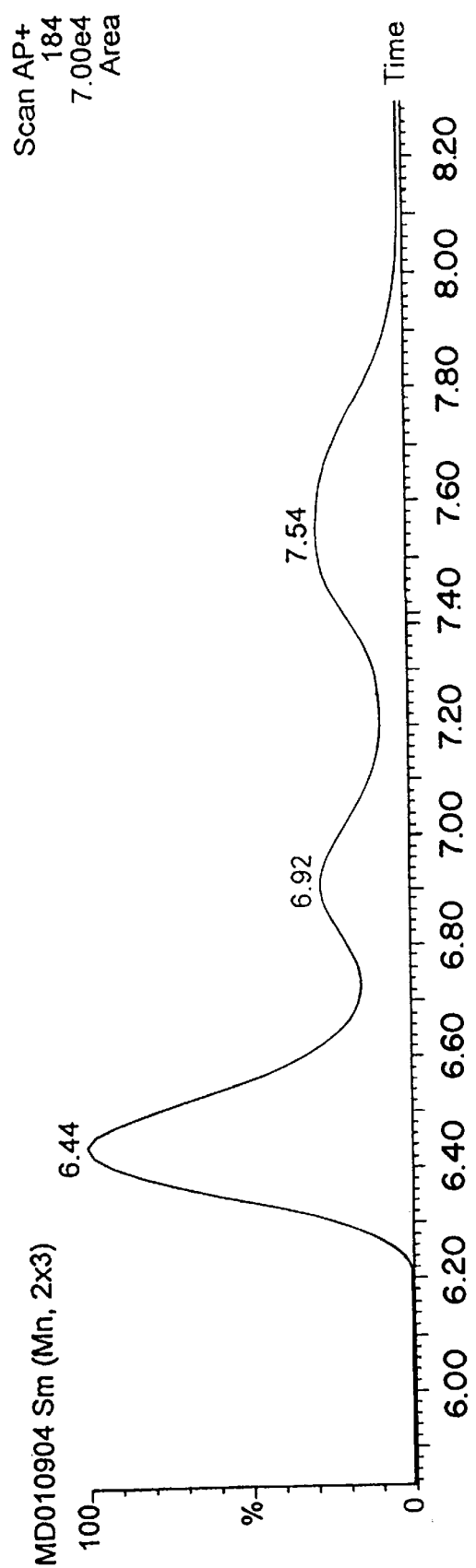
FIG. 3 is the mass spectral data obtained by HPLC/APCI-MS on AM-520.

Mass spectral data obtained by APCI+ on column fractions. Chromatograms (FIG. 3) show the coincidence of these fragments in the spectra.

The 337 dalton fragment is the aglycone without the 3 hydroxy group and phosphocholine moiety. The fragment may be the I-steroid. The peak intensity is relatively small. The 184 dalton fragment is derived from the phosphocholine. The other fragments confirm the breakdown of the phosphocholine.

This compound would be formed by dehydration of AM-538. Because of the extended conjugation, there should be a UV peak about 260 nm. A peak at that wavelength is present., coincidental with the observed mass ions.

The intermediate could be bound to CoA and hydrolysed. The lactone could form spontaneously, but there may be an enzyme to speed the process.

AM-520 would then be reduced in two steps to produce AM-524.

Proposed structure for AM-522(β):
R = Phosphocholine 522 daltons - the mass ion
544 daltons - the sodium salt
485 daltons - loss of NMe3 from choline
339 daltons - loss of phosphocholine

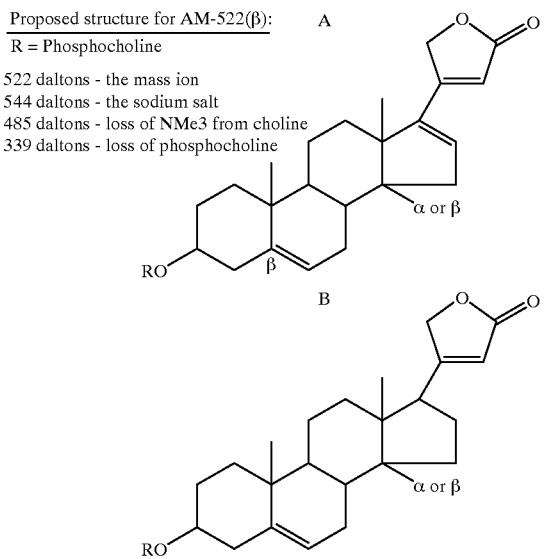

Figures 4C, 4D:
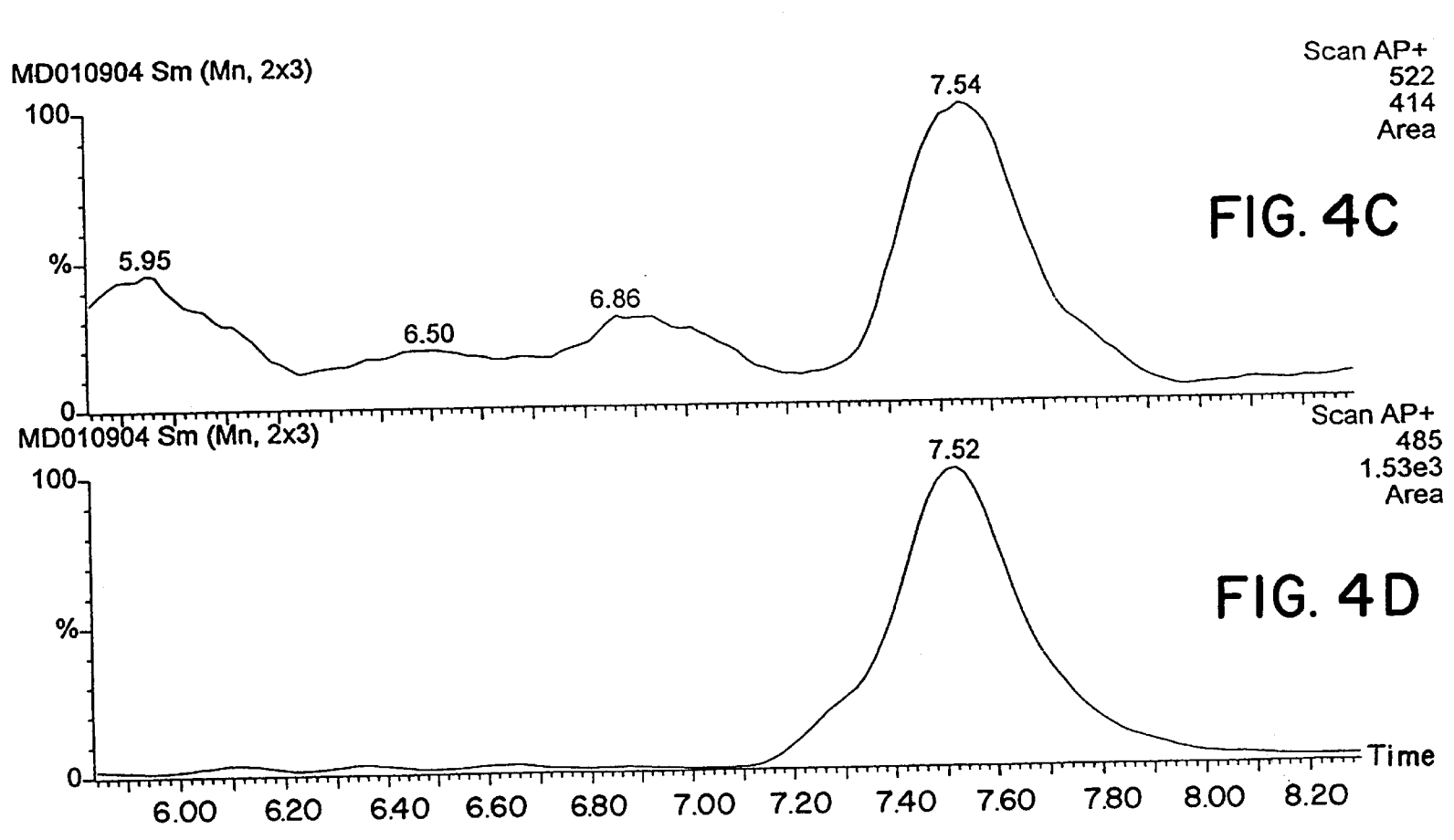
Figure 4E:
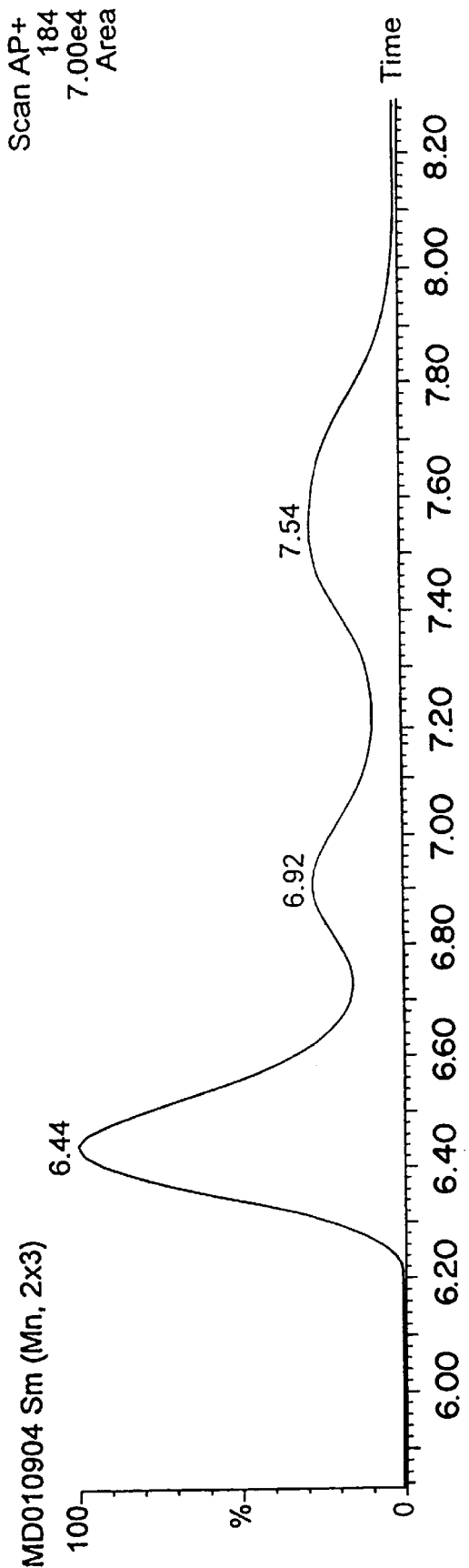
FIG. 4 is the mass spectral data obtained by HPLC/APCI-MS on AM-522.

Mass spectral data obtained by APCI+ on column fractions. Chromatograms (FIG. 4) show the coincidence of these fragments in the spectra.

The 339 dalton fragment is the aglycone without the 3 hydroxy group and phosphocholine moiety. The fragment may be the I-steroid. The peak intensity is relatively small. The 184 dalton fragment is derived from the phosphocholine. The other fragments confirm the breakdown of the phosphocholine.

Compound A would be formed by reduction of the A ring and leave intact the extended conjugation in Ring E. This would lead to a UV peak at 260 nm. A peak at that wavelength is present, coincidental with the observed mass ions. The assignment of 5β reduction is based on the corresponding structures of digoxin and ouabain which are also 5β reduced.

Compound B would be formed by reduction of the D ring. This would lead to elimination of the extended conjugation and loss of the 260 nm peak. Several such compounds were detected in the HPLC chromatographs.

The choice of which compound is reduced first could be determined by the respective enzyme binding characteristics.

Proposed structure for AM-524 (α):
R = phosphocholine 524 daltons - the mass ion
546 daltons - the sodium salt
487 daltons - loss of NMe3 from choline
341 daltons - loss of phosphocholine
(I-steroid)

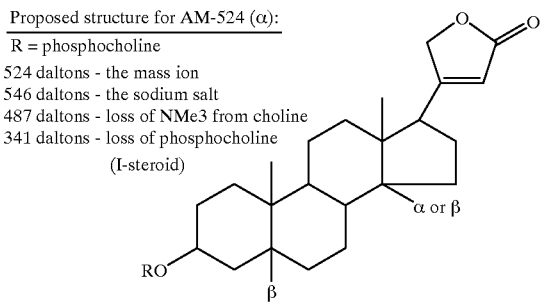

Figures 5A, 5B:
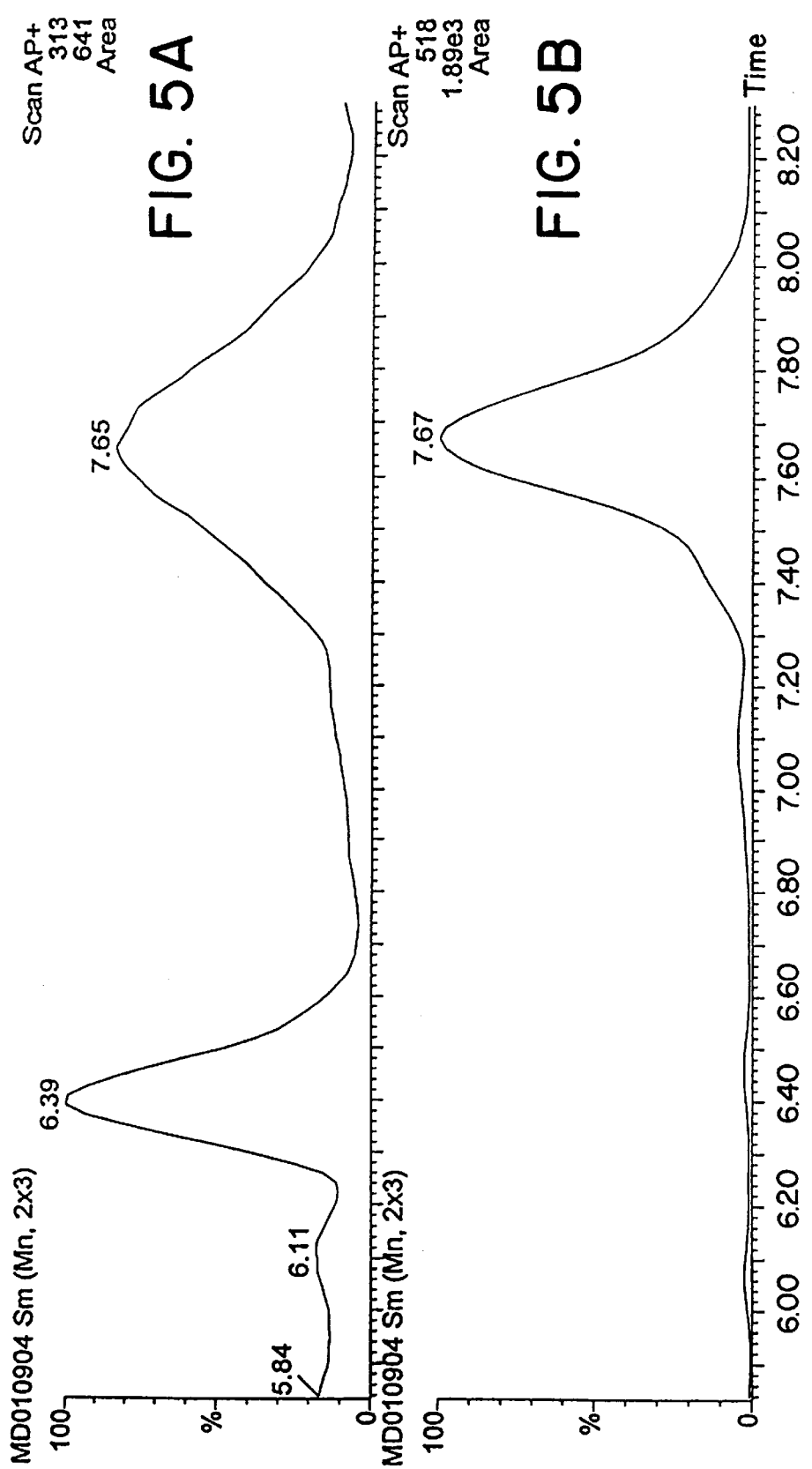
FIG. 5 is the mass spectral data obtained by HPLC/APCI-MS on AM-524.
Figure 5E:
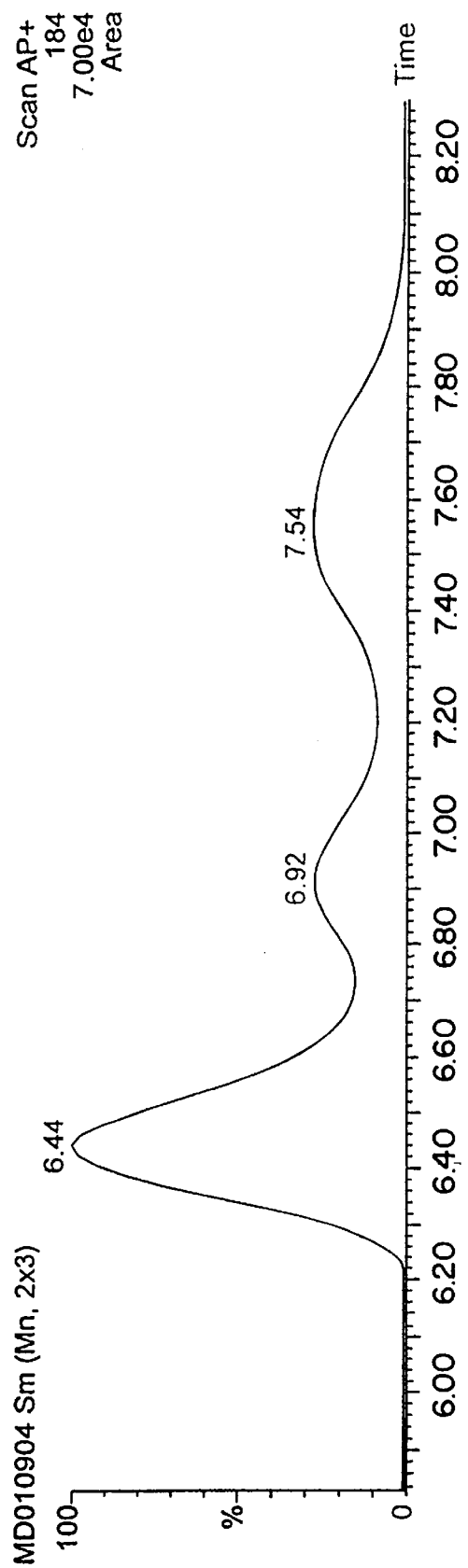

Mass spectral data obtained by APCI+ on column fractions. Chromatograms (FIG. 5) show the coincidence of these fragments in the spectra.

Further confirmed by UV spectra with peak at 220 nm, which is characteristic of the cardenolide structure. Note the absence of the 14 hydroxy group and the tentative assignment of 14α hydrogen on the bridge. This assignment chosen to be the same as that of other steroid hormones. Also note the assignment of the 5β hydrogen on the basis of the similar structure in the other members of the cardenolide series. The 341 dalton peak corresponds to loss of the phosphocholine and could be the I-steroid derivative.

When reacted with acetic anhydride in pyridine, a derivative is formed with a mass ion at 628 daltons. Acetic anhydride would react with the lactone to form an ester and a free carboxylic acid. The compound with the carboxylate anion would not be detected in the cation spectra. To be detected as a cation, the carboxylate would have to be the sodium salt. The combination of the ester and the sodium salt would add 82 daltons to the mass, exactly as observed. This derivative indicates that there can be no other free hydroxyl groups in the molecule, for example, no sugars can be coupled at the three position of the aglycone.

The phosphocholine is confirmed by the fragmentation pattern. The presence of a 184 dalton fragment is characteristic, along with the fragments corresponding to loss of trimethylamine from the sodium salt. In the negative ion spectra, the largest mass corresponds (509 daltons) to loss of methyl and the base ion derives from complete loss of choline (loss of 87 dalton fragment—leaving a major fragment at 437 daltons).

AM-524 cross-reacts with digoxin specific antibodies. AM-524 is present in serum from all species tested (human, mouse, rat, goat, cattle).

Proposed structure for AM-540:
R = Phosphocholine 540 daltons - the mass ion
562 daltons - the sodium salt
503 daltons - loss of NMe3 from choline
357 daltons - loss of phosphocholine
(I-steroid)

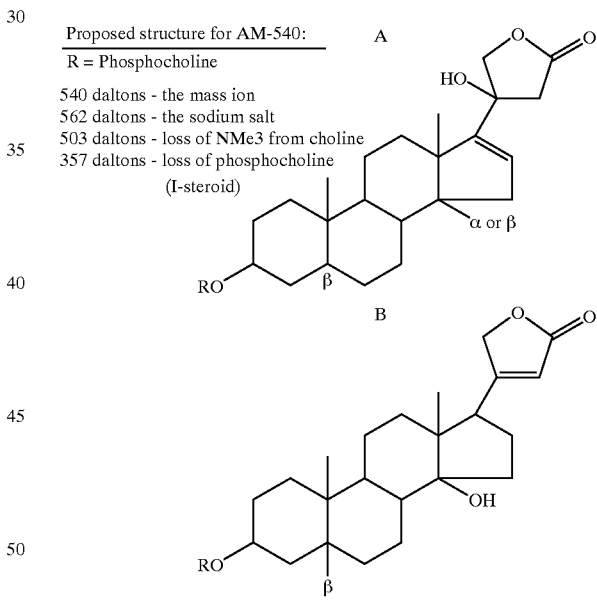

Figure 6A:
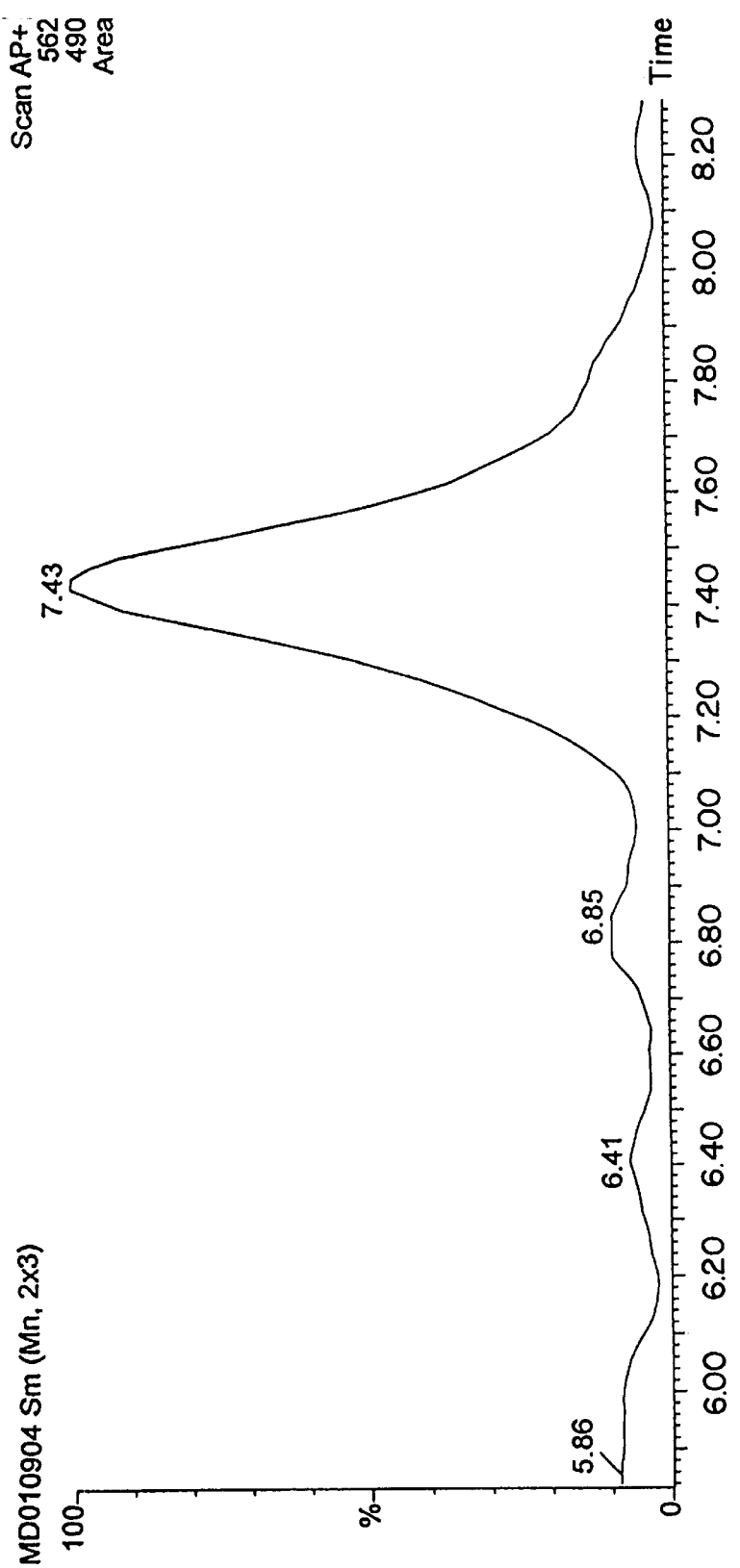
FIG. 6 is the mass spectral data obtained by HPLC/APCI-MS on AM-540.
Figure 6B:
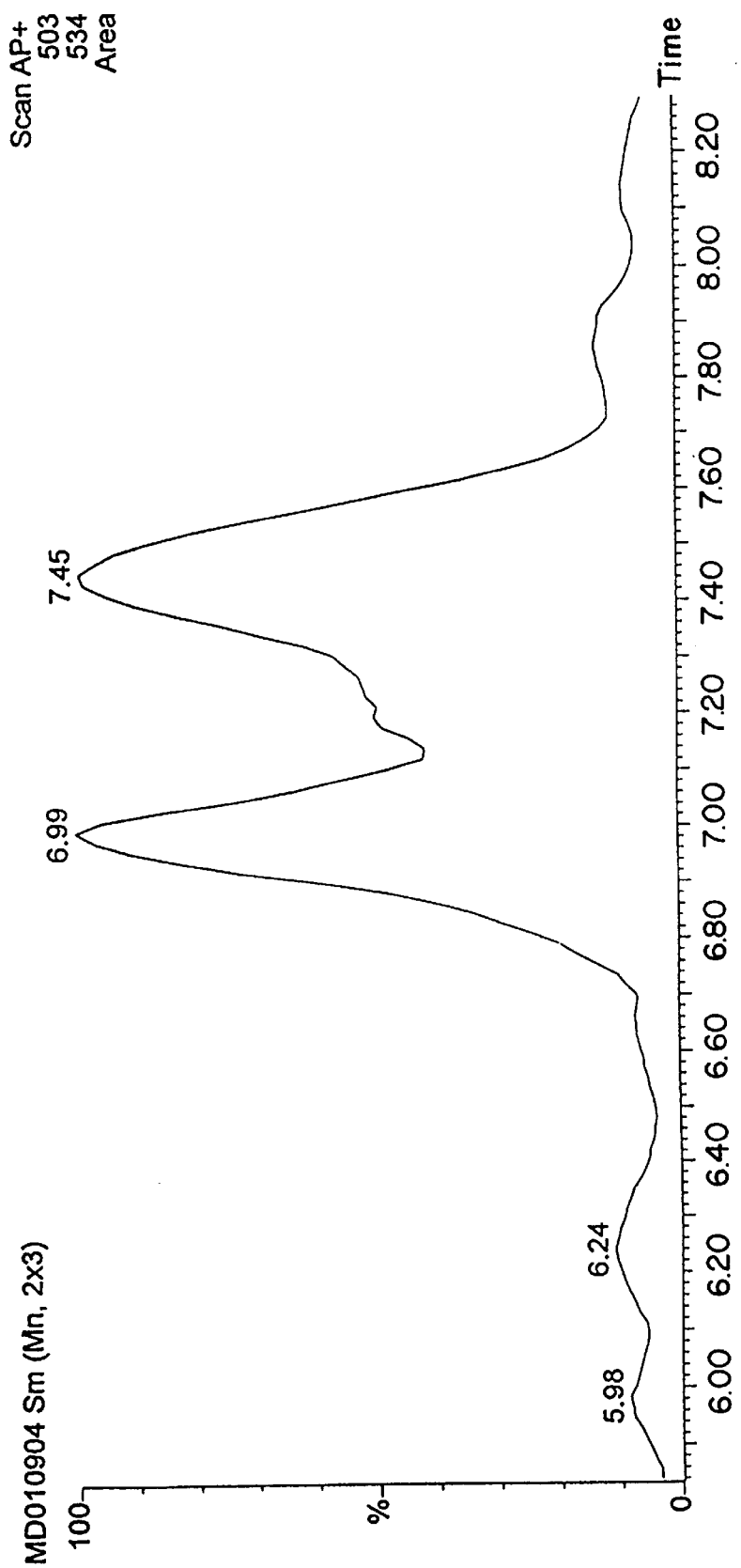
Figure 6C:
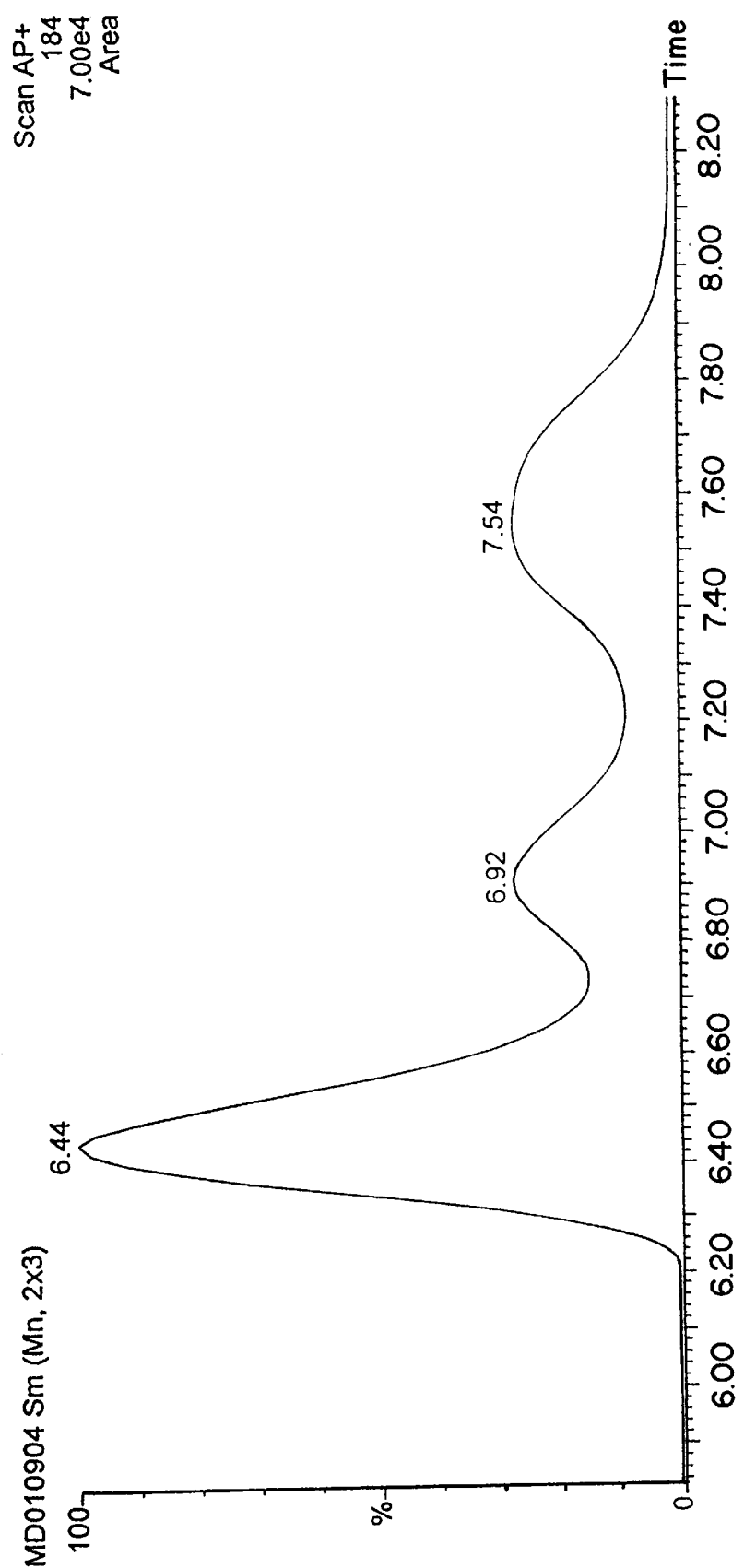

Mass spectral data obtained by APCI+ on column fractions. Chromatograms (FIG. 6) show the coincidence of these fragments in the spectra.

The 357 dalton fragment would be the aglycone without the 3 hydroxy group and phosphocholine moiety, but it was not observed. The 184 dalton fragment is derived from the phosphocholine. The other fragments confirm the breakdown of the phosphocholine.

Both structures shown should generate the observed fragmentation patterns. However, structure A would be a precursor for AM524 while structure B would be a further metabolite, perhaps most like digoxin. The B structure requires the activity of a 14 hydroxylase which has not been reported in mammalian systems. The two possibilities could be resolved by examination of the UV spectrum of the pure material because B should have a UV peak at 220 nm but A should not. The aglycone portion of B has been reported, but not conjugated to phosphocholine.

The hydroxy group is not limited to the 14 position. The observed material could be a metabolite on the degradative pathway, rather than the most active cardiotonic compound.

EXAMPLE 2

Assay for Anti-hypertensive Activity

Sprague-Dawaley rats, weighing 270–300 grams, will be used in all experiments. Rats will be anesthetized with a single intraperitoneal (ip) injection of pentobarbital, 30–40 mg/kg body weight. Polyethylene catheters will be injected into the carotid artery, left external jugular vein and bladder. Upon completion of the surgical procedure, the animals will be given a priming injection of 0.15 M NaCl solution equal to 0.5% body weight. In order to monitor renal function, an infusion of 0.15 M NaCl solution will be started at 0.045 ml/min and containing $^{14}$C-inulin and $^{3}$H-PAH (para-aminohippuric acid, New England Nuclear, Boston, Mass.) in quantities designed to provide 5 microCi per hour and 10 microCi per hour of the 2 radioactive isotopes, respectively. After an equilibration period of 40–50 minutes, the experiment will be commenced.

The intra-arterial blood pressure will be recorded using a transducer and a 8-channel physiography (Beckman, Palo Alto, Calif.). The pressure tracing will be calibrated using a manual sphygmomanometer. Hematocrit values will be measured by routine techniques well known in the art. The plasma and urinary activity of $^{14}$C-inulin-$^{3}$H-PAH will be measured using a beta scintillation counter (Packard Tricarb, Packard Instruments, Chicago, Ill.) The plasma electrolytes will be measured using a flame photometer (Klinaflamer, Beckman Instruments, Palo Alto, Calif.). The glomerular filtration rate (GFR) and renal blood flow will be calculated from the $^{14}$C-inulin and $^{3}$H-PAH clearances, respectively, using standard equations.

AM-524, AM-540, AM-496 and a digoxin control will be administered intravenously at concentrations ranging between 0.01 µg/kg and 10 µg/kg body weight. Blood pressure will be recorded continuously for the duration of the study.

EXAMPLE 3

Reactivity of the Phosphocholinate Cardenolide Compounds of the Present Invention with Digoxin-Specific Antibodies A typical assay will be performed as follows. Standard solutions, containing known amounts of digoxin, will be prepared by diluting standards provided by the manufacturer (Dupont, Boston). Standard curves will be prepared by adding 0.1 ml of standard solutions containing 0.05, 0.1, 0.2, 0.5, 1.0 and 2.0 ng/ml of digoxin to 12×75 mm borosilicate culture tubes (Fisher Scientific Co.) and assaying as described below.

Samples of AM-524, AM-540 and AM-495 are pipetted into 12×75 mm culture tubes and evaporated to dryness under a stream of nitrogen. 0.2 ml of [$^{125}$I]-labeled digoxin-tracer and 0.2 ml of digoxin antibody are added to each tube. The tubes are mixed by vortex and allowed to incubate for 30 minutes at room temperature. Thereafter, the tubes are centrifuged at 2600× g at 4° C. for 30 minutes and transferred to foam decanting racks (Diagnostic Products, Los Angeles, Calif.) and decanted. Each tube will be blotted and the amount of [$^{125}$I] is determined using a gamma counter (Model 1275 Minigamma, LKB, Gaithersburg, Md.). Individual values of digoxin are determined by interpolation against the standard curve obtained at the same time using a smooth line best fit program from LKB and are expressed as ng digoxin equivalents, as described above.

EXAMPLE 4

Distribution of Phosphocholinate Cardenolides Obtained From Normal Women and Women Suffering From PMS Serum samples will be obtained from women suffering from PMS and unaffected control women at different times in their menstral cycle (i.e. before, during and after). The serum samples will be processed as described above and analyzed by LC-MS for the presence of the compounds of the present invention. Any difference in the levels of any one of the compounds of the present invention greater than two standard deviations can be considered a positive diagnosis of PMS. It is expected that women suffering from PMS will have cyclic fluctuations in their serum levels of the compounds of the present invention, mirroring the episodes of their symptoms.

EXAMPLE 5

Distribution of Serum Phosphocholinate Cardenolides Obtained From Normal Individuals and Hypertensive Patients and their Families Genes related to the synthetic pathway for the phosphocholineate compounds of the present invention can be identified by determining the ratios of AM-496, AM-520, AM-522 and AM-524 and AM-540 in individuals and their family members. Serum samples will be obtained from normal individuals and those suffering from hypertension, hypotension, renal disorders (e.g. nephritis or polycystic disease) salt-wasting disorders (e.g. hyperaldosteronism, hydroxylase deficiency, Addison's disorder) (hereinafter alternatively referred to as the proband) and their family members. The samples will be extracted with acetonitrile and subjected to LC-MS as described above. Ratios of AM-496 to AM-524, AM-520, AM-522, and AM-540 will be determined. If the proband had normal ratios the family would not be further investigated or can be used as a control family. If the proband had abnormal ratios, then the family members will be investigated. If the disorder of the proband was also present in some of the family members, then the relationship between the two events will also be determined. If the disorder itself cannot be identified in family members, the abnormal ratio pattern might be present. This could be used for risk assessment as well as for genetic studies.

What is claimed is:

1. A pharmaceutical formulation comprising a compound having the formula

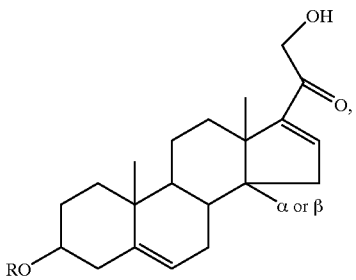

and
a pharmaceutically acceptable carrier diluent,
wherein R=phosphocholine.

2. A method for treating a mammal suffering from hypertension comprising administering to a mammal in need of such treatment an effective amount for treating hypertension of a compound having the formula

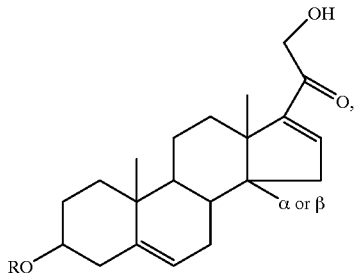

wherein
R=phosphocholine.

3. A method for treating a mammal suffering from polycystic kidney disease comprising administering to a mammal in need of such treatment a disease treatment effective amount of a compound having the formula

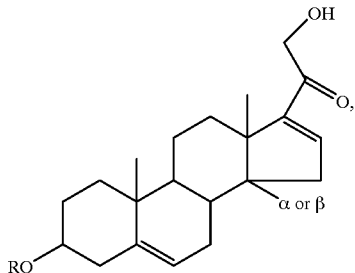

wherein
R=phosphocholine.

4. A method for treating a patient suffering from PMS comprising administering to a mammal in need of such treatment an effective amount for treating PMS of a compound having the formula

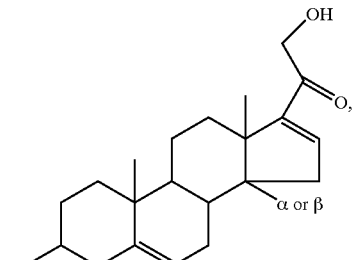

wherein
R=phosphocholine.

5. A method for treating a mammal suffering from preeclampsia comprising administering to mammal in need of such treatment an effective amount for treating pre-eclampsia of a compound having the formula

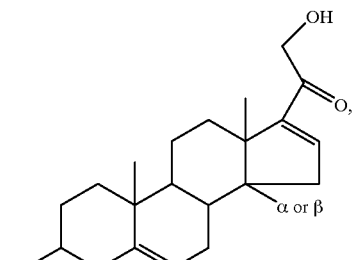

wherein
R=phosphocholine.

* * * * *